US00RE38377E

(19) United States
(12) Reissued Patent
Geshay

(10) Patent Number: US RE38,377 E
(45) Date of Reissued Patent: Jan. 6, 2004

(54) PACKAGE FOR BEVERAGES

(76) Inventor: James F. Geshay, 1500 Flett Ave., Racine, WI (US) 53405

(21) Appl. No.: 10/146,289

(22) Filed: May 15, 2002

Related U.S. Patent Documents

Reissue of:
(64) Patent No.: 6,062,431
Issued: May 16, 2000
Appl. No.: 09/327,216
Filed: Jun. 7, 1999

U.S. Applications:
(60) Provisional application No. 60/088,550, filed on Jun. 8, 1998.

(51) Int. Cl.[7] ..... B65D 35/56
(52) U.S. Cl. ..... 222/105; 222/465; 222/511; 222/1; 229/117.3; 229/117.35; 53/449; 221/96
(58) Field of Search ..... 222/93, 105, 183, 222/465.1, 482, 565; 221/96; 229/117.3, 117.35; 53/175, 449

(56) References Cited

U.S. PATENT DOCUMENTS 2,454,919 A * 11/1948 Hagan ..... 229/117.3
3,233,817 A 2/1966 Casady
3,349,960 A 10/1967 Ketler
4,541,526 A 9/1985 Berg et al.
5,050,775 A 9/1991 Marquardt
5,176,313 A * 1/1993 Curry et al. ..... 229/125.15
5,715,992 A 2/1998 Andrews, Sr. et al.
5,826,752 A 10/1998 Latimer
5,909,841 A 6/1999 Andrews, Sr. et al.
6,062,431 A 5/2000 Geshay
6,196,452 B1 3/2001 Andrews, Sr. et al.
6,290,124 B2 9/2001 Andrews, Sr. et al.

* cited by examiner

*Primary Examiner*—Gene Mancene
*Assistant Examiner*—Patrick Buechner

(57) ABSTRACT

An improvement to a beverage package that includes a flaccid beverage bag, a carton around the bag and a fill spout and dispensing device attached to the bag. The improvement wherein the carton is collapsible and includes front and rear panels with first and second spaced-apart side panels extending between the front and rear panels thereby forming a rectangular upper opening bounded by the panels. Furthermore, a spout securing panel is received in the opening and has the spout extending therethrough, and a cover panel is over the securing panel. A method for transporting and dispensing a beverage is also disclosed.

21 Claims, 3 Drawing Sheets

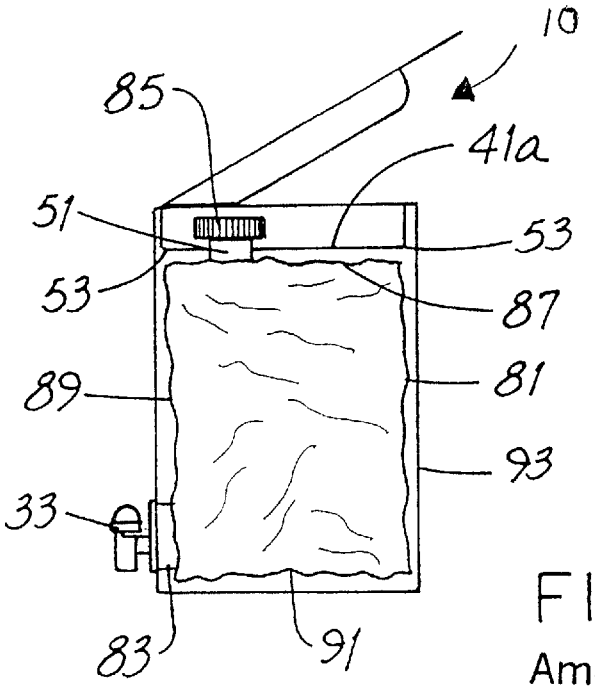
FIG. 4
Amended

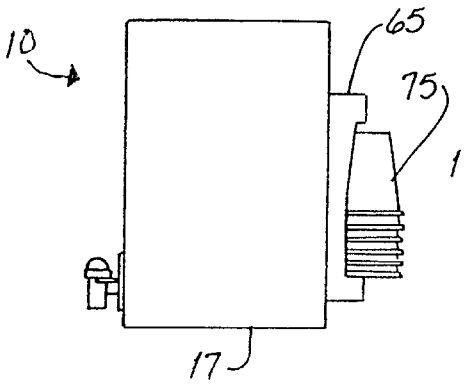
FIG. 5
Amended
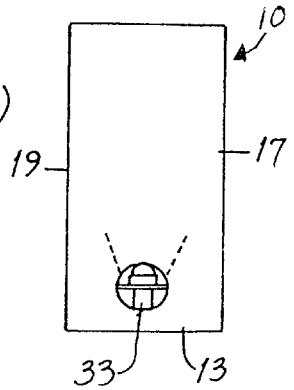
FIG. 7
Amended
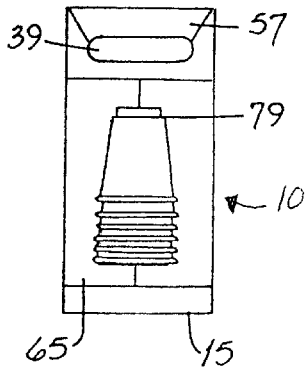
FIG. 8
Amended
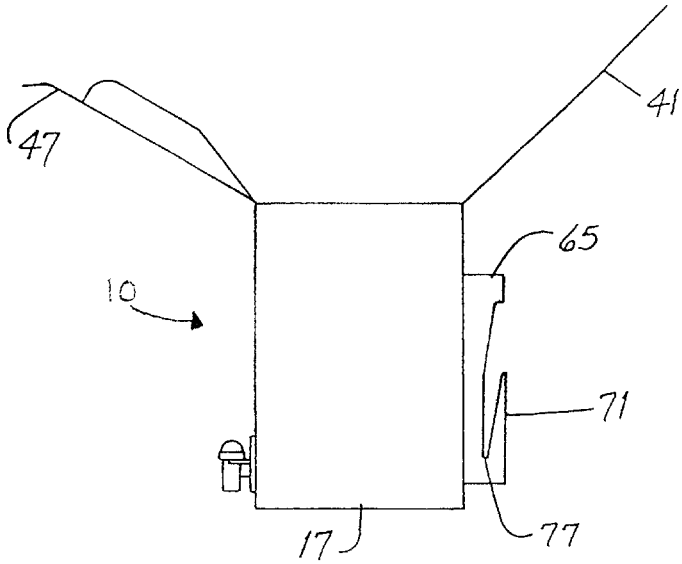
FIG. 6
Amended

PACKAGE FOR BEVERAGES

Matter enclosed in heavy brackets [ ] appears in the original patent but forms no part of this reissue specification; matter printed in italics indicates the additions made by reissue.

RELATED APPLICATION

This application is based upon U.S. provisional patent application Ser. No. 60/088,550 filed Jun. 8, 1998.

FIELD OF THE INVENTION

This invention relates generally to a beverage container and, more particularly, to a method and apparatus for transporting and dispensing a beverage.

BACKGROUND OF THE INVENTION

Gourmet coffee shops have gained a large share of the beverage market in recent years. These shops typically sell individual servings of upscale brands of coffee. These servings are usually packaged in single serving cups that are suitable for carry-out orders.

These gourmet coffee shops have so changed to public's taste for coffee that such coffee is now being requested as part of a coffee service for large gatherings such as meetings and the like. One impediment to the serving of gourmet coffee in large gatherings, however, is the absence of a container large enough to efficiently transport and serve the beverage outside of the coffee shop. Therefore, an apparatus that wound allow one to transport and serve more than one cup of coffee at a time would be an important advancement in the art.

SUMMARY OF THE INVENTION

This invention is related to an improved beverage package that includes a flaccid beverage bag, a carton around the bag and a fill spout and dispensing device attached to the bag. The improvement involves a carton that includes front and rear panels and first and second spaced-apart side panels which extend between the front and rear panels so as to form a rectangular upper opening bounded by the panels. A spout securing panel with the spout extending therethrough is received in the opening and a cover panel is placed over the securing panel.

In one embodiment of the invention, a cup retention panel that includes a cup retaining projection is attached to and spaced outwardly from the carton. In another embodiment, the front panel includes an aperture and the dispensing device protrudes through the aperture. In a more specific version of such embodiment, the flaccid beverage bag has a top and bottom portion that encloses the bag so as to define an interior and an exterior section. The fill spout is connected in flow communication with the top portion of the beverage bag and the dispensing device, which is connected near the bottom portion of the beverage bag in flow communication with the interior, protrudes through the aperture.

In a preferred embodiment of the invention, a spring-closed spigot is attached to the dispensing device. In the most preferred embodiment, the carton includes a carrying handle. In still another embodiment, the spout securing panel has a first width, the front and rear panels have a second width, and the second width is greater than the first width. A preferred version of all of the embodiments is one in which the package is collapsible.

The carton used in the invention is formed from a foldable blank that is comprised of a front panel and a rear panel that are substantially parallel to each other. These panels each have an interior and exterior surface and the front panel includes a flap that has a scored aperture at one end while the rear panel includes a scored carry-handle cutout. The blank also has a first side panel and a second side panel which are substantially parallel to each other and extend between the front panel and the rear panel in such a manner that a slit is formed between the rear panel and the second side panel. A cover panel having a latch flap is attached to the front panel and a cup retention panel extends from the rear panel. The cup retention panel includes a lock tab that is suitable for insertion in the slit.

The blank also has a first glue tab that adheres to the interior surface of the rear panel. Such tab extends along the first side panel. Furthermore, a first glue flap extends from the front panel and adheres to a third glue flap that extends from the first side panel. A second glue flap extends from the rear panel and adheres to a fourth glue flap that extends from the second panel. The second and fourth glue flaps interlocking with the first and third glue flaps in order to form the bottom of the carton.

In one embodiment, the carton includes a spout securing panel that has a scored opening that is integrated with and extends from the rear panel. In a specific version of such embodiment, the front and rear panels have a first width, the securing panel has a second width, and the first width is greater than the second width.

In another embodiment, a separate spout securing panel having a scored opening is positioned between the front and rear panels. In still another embodiment, a cup retaining projection is attached to the cup retention panel.

In a preferred embodiment of the invention, a series of scored lines are positioned between the front panel and the first side panel, the front panel and the second side panel, the second side panel and the rear panel, and the rear panel and the cup retention panel.

The invention also includes a method for transporting and dispensing a beverage in a beverage package that includes a flaccid beverage bag, a carton around the bag and a fill spout and dispensing device. The transporting method is comprised of the steps of: (1) squaring-up a prefolded carton so that the carton has a top portion, a bottom portion, a front panel, a rear panel, and a first and second side panel; (2) positioning a spout securing panel having an opening in the top of the carton; (3) placing the fill spout in the opening in the spout securing panel; (4) installing the dispensing device through an aperture in the front panel; (5) filling the bag through the fill spout with a beverage; (6) inserting a latch flap attached to the top portion in a carry-handle located in the rear panel; (7) carrying the carton via the carry-handle to a desired location, and (8) dispensing the beverage through the dispensing device into a beverage serving apparatus.

BRIEF DESCRIPTION OF THE DRAWINGS

FIG. 4 is a cutaway side elevation view of the new package with the cover panel in an intermediate position.

FIG. 5 is a side elevation view of the new package in full representation and with cups mounted on the cup retention panel.

FIG. 6 is a side elevation view of the new package in full representation and with no cups mounted on the cup retention panel.

FIG. 7 is a front elevation view of the new package.

FIG. 8 is a rear elevation view of the new package with cups mounted on the cup retention panel.

DETAILED DESCRIPTIONS OF PREFERRED EMBODIMENTS

Figure 1:
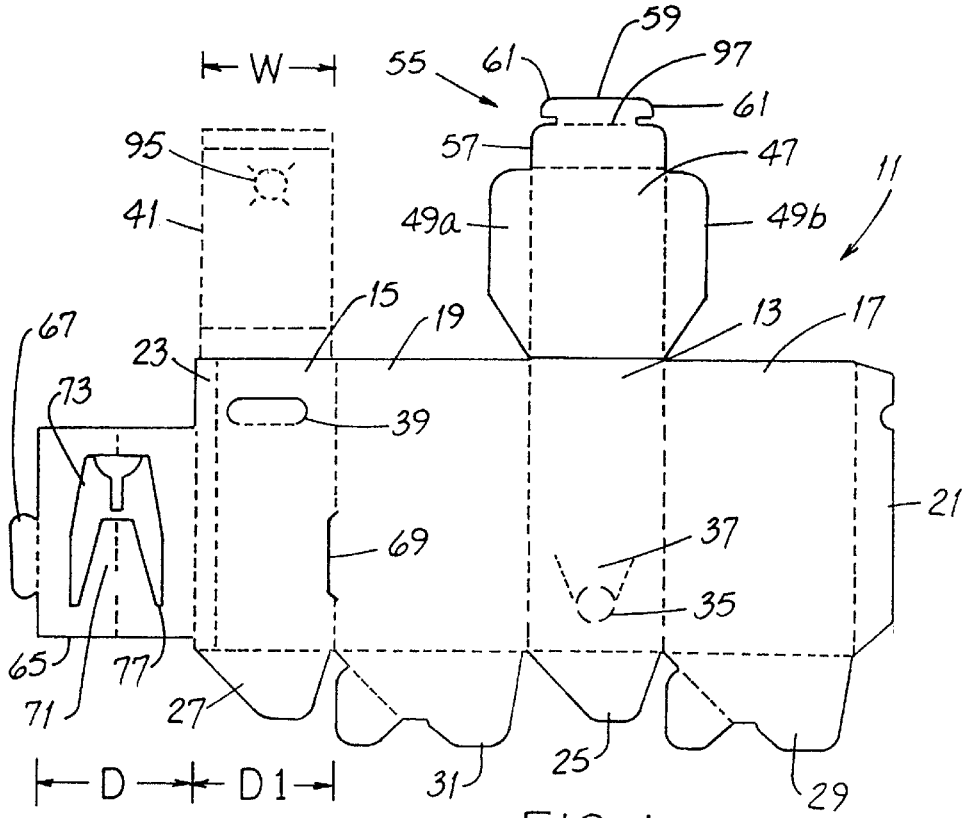
FIG. 1 is a plan view of a corrugated cardboard blank used to make the new package. Fold lines are shown in dashed line as is a spout securing panel optionally integral with the blank.

Before describing the new beverage package 10, this specification first explains aspects of the blank 11 used to make such package. FIG. 1 shows a highly preferred blank 11, preferably made of corrugated cardboard, which includes panels 13 and 15 which form the front and rear panels, respectively, of the package 10 when the carton and bag are set up for use. The blank 11 also has first and second side panels 17 and 19, respectively, and such panels 17, 19 extend between the front and rear panels 13, 15 when the carton and bag are set up for use. In the erected package shown in FIGS. 5, 7 and 8, the panels 13, 15 are generally parallel to one another and the panels 17, 19 are generally parallel to one another.

Figure 2:
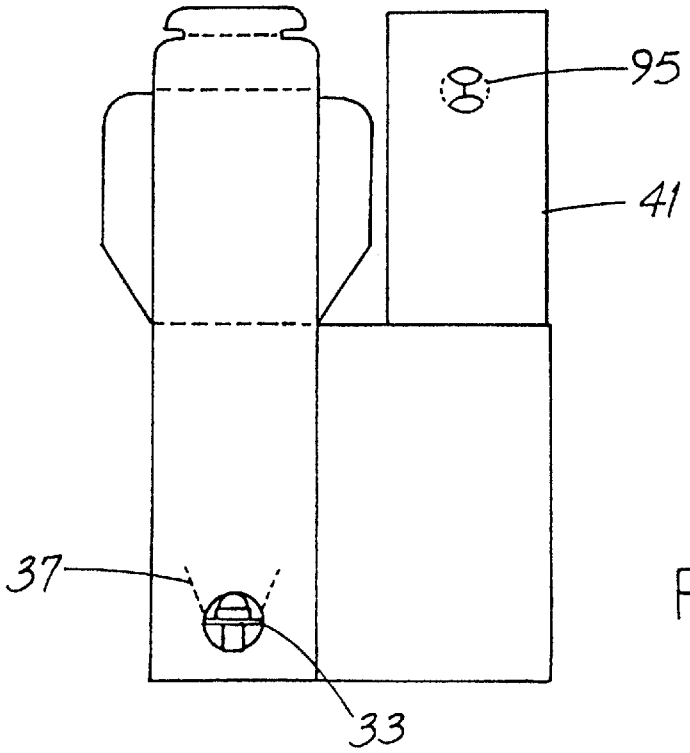
FIG. 2 is a plan view of the new package in its knocked-down or "fold-flat" configuration for shipping.

A glue tab 21 extends along the panel 17 and when the carton is partially assembled in a "flat-fold" configuration for shipping as shown in FIG. 2, the tab 21 is glued to the interior surface of the panel 15 generally along the strip 23. Similarly, first and second glue flaps 25, 27, respectively, extend from the panels 13, 15, respectively, and third and fourth glue flaps 29, 31, respectively, extend from the panels 17, 19, respectively. In a specific, highly preferred embodiment, the first and second flaps 25, 27 have substantially identical shapes that are [substantially identical to one another and] different from that of the flaps [25, 27] *29, 31*. In the flat-fold configuration, the flaps 27, 31 are glued to one another and the flaps 25, 29 are glued to one another. (As will become apparent, the flaps 25, 27, 29, 31 are shaped and glued in such a way that all four flaps 25, 27, 29, 31 interlock to form the bottom of the package 10. Configuring and gluing such flaps 25, 27, 29, 31 is know*n* per se.)

To accommodate the dispensing device 33, the panel 13 includes a scored aperture 35 and flap 37. In the flat-fold configuration or when the carton is erected for use, the scored aperture 35 is pushed out, the flap 37 released, the dispensing device 33 inserted through the resulting opening and the flap 37 restored to its original position. The blank 11 also includes a scored carry-handle cutout 39 which is pushed out when the carton is erected for use.

Figure 3:
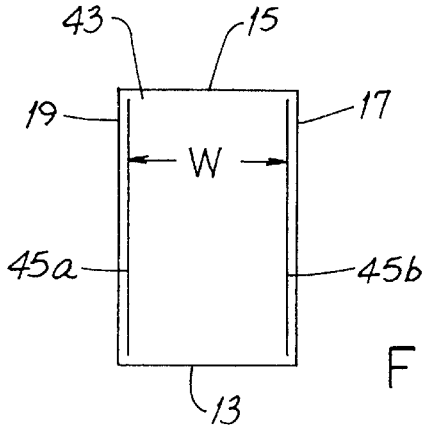
FIG. 3 is a representative top plan view of the carton showing the relative width of the spout securing panel with respect to the widths of the front and rear carton panels.

Referring also to FIGS. 4, 7 and 8, in a highly preferred embodiment, the blank 11 includes a spout securing panel 41 integral with and extending away from the panel 15. Referring also to FIG. 3, the width "W" of the panel is preferably slightly less than the width of either of the panels 13, 15 so that when the spout securing panel 41 is folded into the rectangular upper opening 43, clearance slots 45a, 45b are defined between the securing panel 41 and the panels 19, 17, respectively. When the cover panel 47 is folded over the securing panel 41, the slots 45a, 45b, receive the wings 49a, 49b, respectively, of the cover panel 47. The securing panel 41 includes a scored opening which receives the fill spout 51 therethrough when the package 10 is erected for use.

As described above, the spout securing panel 41 is preferably an integral part of the blank 11. In another embodiment, such panel 41a may be separate from the blank 11 and simply folded along fold lines 53 and urged into the opening 43 to secure the fill spout 51.

The blank 11 also includes the cover panel 47 integral with and extending away from the panel 13. Such cover panel 47 includes, in addition to the wings 49a, 49b a latch flap 55 having first and second [compartments] *components* 57, 59, respectively. The second component 59 has fold-scored ears 61 so that such component 59 may be inserted inwardly through and locked to the carry-handle cutout 39 when the package 10 is erected for use.

Configured as described above, the blank 11 has great utility in making the new package 10. However, a feature highly convenient for sellers and purchasers of "take-out" coffee involves the cup retention panel 65. In a specific embodiment, such panel 65 is integral with the blank 11 and extends laterally away from the panel 15. The retention panel 65 includes a lock tab 67 inserted through a slit 69 at the boundary shared by the panels 15 and 19. The dimension "D" of the retention panel 65 is slightly greater than the dimension D1 of the panel 15 so that when the package 10 is erected for use and the lock tab 67 is in the slit 69, the retention panel 65 bows outwardly from the panel 15 and is spaced therefrom as shown in FIGS. 5 and 6.

The retention panel 65 includes a cup retaining projection 71 defined in part by an inverted V-shaped opening 73 therearound. As the package 10 is being filled and otherwise prepared for the customer, a quantity of nested cups 75 is urged downwardly over the projection 71. Such cups 75 are retained on the carton by the projection 71 and by a slight compression fit between the notches 77, which engage the lip of the lowermost cup 75, and the ridge 79 which engages the upwardly extending edge of the uppermost cup 75. (It is no doubt appreciated that when a cup 75 is taken from the package 10 for use, such cup 75 is uprighted.)

The flaccid bag 81 includes the dispensing device 33 attached thereto in flow communication with the bag interior. A highly preferred dispensing device 33 has a spring-closed spigot forcefully affixed (to help prevent inadvertent spills) to the device neck 83. The bag 81 also has the fill spout 51 attached thereto *i*n flow communication with the bag interior. The fill spout 51 has a closure 85 attached (or re-attached) after the bag 81 is filled with the beverage. In a specific embodiment, the fill spout 51 is attached to the top member 87 of the bag 81 and the dispensing device 33 is attached to a side member 89 closely adjacent to the bottom member 91.

Assuming that availability of the blank 11 and the bag 81 and further assuming that the glue tab 21 is adhered to the panel 15 along the strip 23, that the flaps 25, 29 are glued to one another and that the flaps 27, 31 are glued to one another, the bag 81 is urged into the carton 93 and the dispensing device 33 is urged through the scored aperture 35 and flap 37 as generally shown in FIG. 2. In such configuration, the package 10 is in it flat-fold or "knocked-down" intermediate configuration so that the multiple packages 10 can be stacked for shipping in bulk to, e.g., the point of retail sale.

When a customer orders, e.g., a gallon of take-out coffee, the server unfolds the package 10 from the configuration shown in FIG. 2 to a "squared-up" or rectangular configuration. In so doing, the flaps 29, 31 automatically lock together and jut upwardly toward the interior of the carton 93.

The server then inserts the fill spout 51 (with closure factory-attached) through the opening 95 in the spout securing panel 41 or 41a, folds such panel 41 or 41a and urges it downwardly into the now-open rectangular top opening 43 of the carton 93 to the position shown in FIG. 4. Then the bag 81 is filled through the spout 51, the closure 85 is affixed and the wings 49a, 49b of the cover panel 47 are then folded toward one another and inserted downwardly through the slots 45a, 45b.

The ears 61 of the second component 59 of the latch flap 55 are then folded toward one another to permit such second component 59 to be inserted through the cutout 39. Considering the FIGURES, particularly FIGS. 1 and 8, the first component 57 is above the cutout 39 and on the outside of the package 10. The second component 59 is above the cutout 39 and on the inside of the package 10 and the fold line 97 is about in registry with the top edge of the cutout 39. Therefore, the weight of the package 10 and the beverage contained therein is borne by the user's fingers which extend inwardly through such cutout 39. Notably, the first and second components 57, 59 (or one of them) are "pinched" or somewhat compressed between the fingers and the upper edge of the cutout 39, thereby additionally securing the cover panel 47 in place.

While the principles of the invention have been shown and described in connection with preferred embodiments, it is to be understood clearly that such embodiments are by way of example and are not limiting.

What is claimed:

[1. In a beverage package including a flaccid beverage bag, a carton around the bag and a fill spout and dispensing device attached to the bag, the improvement wherein:

the carton includes front and rear panels and first and second spaced-apart side panels extending between the front and rear panels and forming a rectangular upper opening bounded by the panels;

a spout securing panel is received in the opening and has the spout extending therethrough; and a cover panel is over the securing panel.]

[2. The package of claim 1 including:

a cup retention panel attached to and spaced outwardly from the carton and including a cup retaining projection.]

[3. The package of claim 1 wherein the front panel includes an aperture; and the dispensing device protrudes through the aperture.]

[4. The package of claim 3 wherein:

the flaccid beverage bag has a top portion and a bottom portion and includes an interior and exterior;

the fill spout is connected in flow communication with the top portion of the beverage bag; and the dispensing device connected near the bottom portion of the beverage bag in flow communication with the interior of such bag protrudes through the aperture.]

[5. The package of claim 1 wherein a spring-closed spigot is attached to the dispensing device.]

[6. The package of claim 1 wherein the carton includes a carrying handle.]

[7. The package of claim 1 wherein:

the spout securing panel has a first width;

the front and rear panels have a second width; and the second width is greater than the first width.]

[8. The package of claim 1 wherein the package is collapsible.]

[9. A foldable blank erectable into a carton for transporting a beverage, the foldable blank comprising:

a front panel and a rear panel substantially parallel to each other, said front and rear panels each having an interior surface and an exterior surface and the front panel includes a flap having scored aperture at one end while the rear panel includes a scored carry-handle cutout;

a first side panel and a second side panel substantially parallel to each other and extending between the front panel and the rear panel;

a slit formed between the rear panel and the second side panel;

a cover panel attached to the front panel, said cover panel having a latch flap;

a cup retention panel extending from the rear panel, said cup retention panel having a lock tab suitable for insertion in the slit;

a first glue tab extending along the first side panel, said first glue tab adhering to the interior surface of the rear panel;

a first glue flap extending from front panel adhering to a third glue flap extending from the first side panel;

a second glue flap extending from the rear panel adhering to a fourth glue flap extending from the second panel, said second and fourth glue flaps interlocking with the first and third glue flaps, thereby forming a bottom to the carton.]

[10. The foldable blank of claim 9 wherein a spout securing panel having a scored opening is integrated with and extends from the rear panel.]

[11. The foldable blank of claim 10 wherein:

the front and rear panels have a first width;

the securing panel has a second width; and the first width is greater than the second width.]

[12. The foldable blank of claim 9 wherein a separate spout securing panel having a scored opening is positioned between the front and rear panels.]

[13. The foldable blank of claim 9 wherein a cup retaining projection is attached to the cup retention panel.]

[14. The foldable blank of claim 9 wherein a series of scored lines are positioned between the front panel and the first side panel, the front panel and the second side panel, the second side panel and the rear panel, and the rear panel and the cup retention panel.]

[15. A method for transporting and dispensing a beverage in a beverage package that includes a flaccid beverage bag, a carton around the bag and a fill spout and dispensing device, said method comprised of the steps of squaring-up a prefolded carton so that the carton has a top portion, a bottom portion, a front panel, a rear panel, and a first and second side panel;

positioning a spout securing panel having an opening in the top of the carton;

placing the fill spout in the opening in the spout securing panel;

installing the dispensing device through an aperture in the front panel;

filling the bag through the fill spout with a beverage;

inserting a latch flap attached to the top portion in a carry-handle located in the rear panel;

carrying the carton via the carry-handle to a desired location; and dispensing the beverage through the dispensing device into a beverage serving apparatus.]

*16. A unitary foldable blank erectable into a carton for transporting a beverage, the foldable blank comprising:*

*a front vertical panel and a rear vertical panel, the panels being substantially parallel to each other when the*

*blank is erected, the front and rear vertical panels each having an interior surface and an exterior surface and the front vertical panel includes an aperture at one end;*

*side vertical panels that extend between the front and rear vertical panels when the blank is erected; and*

*a spout-securing panel integral with and extending from one of the vertical panels, the spout-securing panel having a spout-receiving opening.*

*17. The unitary blank of claim 16 further including a cover panel integral with and extending from another one of the vertical panels.*

*18. The unitary blank of claim 16 wherein:*

*the front and rear panels have a first width;*

*the securing panel has a second width; and*

*the first width is greater than the second width.*

*19. The unitary blank of claim 16 wherein:*

*the spout-securing panel is integral with and extends from the rear vertical panel; and*

*the cover panel is integral with and extends from the front vertical panel.*

*20. The unitary blank of claim 19 wherein:*

*the rear panel includes a carry-handle cutout; and*

*the cover panel has a latch flap engageable with the carry-handle cutout when the blank is erected.*

*21. The unitary blank of claim 16 wherein the side vertical panels consist of first and second side vertical panels which, when the blank is erected, are substantially parallel to each other, each extending from the front panel to the rear panel.*

*22. The unitary blank of claim 21 further comprising:*

*a first glue tab that extends along the first side panel and, when the blank is erected, adheres to the interior surface of the rear panel;*

*a first glue flap that extends from front panel and, when the blank is erected, adheres to a third glue flap that extends from the first side panel; and*

*a second glue flap that extends from the rear panel and, when the blank is erected, adheres to a fourth glue flap that extends from the second side panel, the second and fourth glue flaps being interlockable with the first and third glue flaps upon erection of the blank.*

*23. The unitary blank of claim 21 wherein a series of scored lines are positioned between the front panel and the first side panel, the front panel and the second side panel, and the second side panel and the rear panel.*

*24. The unitary blank of claim 21 wherein:*

*a slit is formed between the rear panel and the second side panel; and*

*a cup retention panel extends from the rear panel, the cup retention panel having a lock tab suitable for insertion in the slit when the blank is erected.*

*25. The unitary blank of claim 24 wherein the cup retention panel has a cup retaining projection attached thereto.*

*26. A method for transporting and dispensing a beverage in a package that includes a flaccid beverage bag, a carton around the bag, a fill spout and a dispensing device attached to the bag, the method comprising the steps of:*

*providing a unitary non-erected carton having, as parts of a single piece, (a) front and rear vertical panels, the front panel having an aperture at one end, (b) side vertical panels extending between the front and rear vertical panels, and (c) a spout-securing panel integral with and extending from one of the vertical panels, the spout-securing panel having a spout-receiving opening, the non-erected carton enclosing the flaccid beverage bag with the dispensing device secured through the panel aperture in the front panel;*

*erecting the carton so that it has a top portion and a bottom portion, the erecting step including positioning the integral spout-securing panel at the top portion of the carton and placing the fill spout in the spout-receiving opening;*

*filling the bag through the fill spout with a beverage;*

*carrying the carton to a desired location; and*

*dispensing the beverage through the dispensing device.*

*27. The method of claim 26 further comprising the step of placing a cover on the top portion of the carton.*

*28. The method of claim 27 wherein the cover comprises a cover panel integral with and extending from another one of the vertical panels.*

*29. The method of claim 28 further comprising the step of inserting a latch flap integral with and extending from the cover panel into a carry-handle cutout included in the rear vertical panel.*

*30. A beverage package comprising:*

*a unitary erectable carton that, in erected condition, has (a) a front vertical panel and a rear vertical panel substantially parallel to each other, the front vertical panel having an aperture at one end, (b) side vertical panels extending between the front and rear vertical panels, and (c) a spout-securing panel with a spout-receiving opening, all of such panels being part of a single piece; and*

*a flaccid beverage bag enclosed in the carton, the bag having a fill spout secured through the spout-receiving opening and a dispensing device secured through the aperture.*

*31. The beverage package of claim 30 wherein a spring-closed spigot is attached to the dispensing device.*

*32. The beverage package of claim 30 wherein:*

*the unitary erectable carton includes a cup retention panel that is integral with the carton; and*

*the carton, in erected condition, has the cup retention panel extending outward from the carton.*

*33. The beverage package of claim 30 wherein the rear panel includes a carry-handle cutout.*

*34. The beverage package of claim 30 wherein the side vertical panels consist of first and second side vertical panels and the unitary erectable carton further comprises:*

*a first glue tab extending along the first side panel that adheres to the interior surface of the rear panel;*

*a first glue flap extending from front panel that adheres to a third glue flap extending from the first side panel; and*

*a second glue flap extending from the rear panel that adheres to a fourth glue flap extending from the second side panel, the second and fourth glue flaps being interlockable with the first and third glue flaps to form a bottom when the carton is in erected condition.*

*35. The beverage package of claim 30 wherein:*

*the vertical panels form an upper opening when the unitary erectable carton is in erected condition; and*

*the spout-securing panel extends into the upper opening.*

*36. The beverage package of claim 35 wherein the unitary erectable carton includes a cover panel that is integral with the carton and wherein the carton, in erected condition, has the cover panel extending over the spout-securing panel.*

* * * * *